(12) United States Patent
Ogawa et al.

(10) Patent No.: US 11,767,284 B2
(45) Date of Patent: Sep. 26, 2023

(54) METHOD FOR PRODUCING UNSATURATED CARBOXYLIC ESTER

(71) Applicant: Mitsubishi Chemical Corporation, Tokyo (JP)

(72) Inventors: Yasushi Ogawa, Tokyo (JP); Risa Katayama, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 478 days.

(21) Appl. No.: 17/034,137

(22) Filed: Sep. 28, 2020

(65) Prior Publication Data

US 2021/0009499 A1    Jan. 14, 2021

Related U.S. Application Data

(63) Continuation of application No. PCT/JP2019/013011, filed on Mar. 26, 2019.

(30) Foreign Application Priority Data

Mar. 28, 2018  (JP) ................................ 2018-061728

(51) Int. Cl.
*C07C 67/08* (2006.01)
*B01J 8/02* (2006.01)

(52) U.S. Cl.
CPC ............. *C07C 67/08* (2013.01); *B01J 8/0242* (2013.01); *B01J 8/0278* (2013.01)

(58) Field of Classification Search
CPC ...... B01D 47/00; B01D 53/005; B01D 53/78; B01J 10/00; B01J 2208/00221; B01J 2231/49; B01J 31/08; B01J 8/0242; B01J 8/0278; B01J 8/0446; B01J 8/0492; B01J 8/0496; B01J 8/06; B01J 8/067; B65B 25/001; B65B 41/14; B65B 41/18; B65B 51/148; B65B 59/00; B65B 61/10; B65B 65/02; B65B 7/164; F16H 19/04
See application file for complete search history.

(56) References Cited

U.S. PATENT DOCUMENTS

| | | | |
|---|---|---|---|
| 2,917,538 A * | 12/1959 | Carlyle | .................. C07C 67/08 560/205 |
| 4,833,267 A | 5/1989 | Nakashima et al. | |
| 5,645,696 A | 7/1997 | Woo et al. | |
| 5,817,865 A | 10/1998 | Machhammer et al. | |
| 5,866,713 A | 2/1999 | Suzuki et al. | |
| 6,072,076 A | 6/2000 | Schmidt et al. | |
| 6,362,364 B1 | 3/2002 | Hirata et al. | |
| 2005/0209481 A1 | 9/2005 | Yada et al. | |

FOREIGN PATENT DOCUMENTS

| | | |
|---|---|---|
| CN | 87 1 05726 A | 7/1988 |
| CN | 1123270 A | 5/1996 |
| CN | 1162591 A | 10/1997 |
| CN | 1165808 A | 11/1997 |
| CN | 1697822 A | 11/2005 |
| CN | 101184720 A | 5/2008 |
| CN | 102344363 A | 2/2012 |
| EA | 006900 B1 | 4/2006 |
| JP | 55-122740 A | 9/1980 |
| JP | 3-52843 A | 3/1991 |
| JP | 08-143512 A | 6/1996 |
| JP | 10-279523 A | 10/1998 |
| JP | 2005-263731 A | 9/2005 |
| JP | 2009-001510 A | 1/2009 |
| WO | WO 2006/134884 A1 | 12/2006 |
| WO | WO2006134884 | * 12/2006 |

OTHER PUBLICATIONS

Japanese Office Action dated Jan. 24, 2023 in Japanese Patent Application No. 2019-059278 (with unedited computer generated English translation) 8 pages.
Indonesian Office Action dated Aug. 2, 2022 in Indonesian Patent Application No. P00202007647 (with English language translation), 4 pages.
Extended European Search Report dated Apr. 12, 2021 in European Patent Application No. 19777801.2, 7 pages.
Chinese Search Report dated Sep. 29, 2022 in corresponding Chinese Patent Application No. 201980022376.3 (with unedited computer generated English translation), 6 pages.
Indian Office Action dated Nov. 12, 2021 in Indian Patent Application No. 202047046318, 5 pages.
Combined Russian Office Action and Search Report dated Sep. 19, 2022 in Russian Patent Application No. 2020135068/04 (with unedited computer generated English translation), 15 pages.
Japanese Office Action dated Jul. 19, 2022 in Japanese Patent Application No. 2019-059278 (with unedited computer generated English translation), 6 pages.

(Continued)

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

An object of the present invention is to provide a method for producing an unsaturated carboxylic ester, wherein the risk of polymerization blockage is reduced and the required equipment cost and workload involved are kept low while maintaining a high conversion rate in an esterification reaction of unsaturated carboxylic acid. This object can be achieved by a method for producing an unsaturated carboxylic ester, which includes performing an esterification reaction using a reactor packed with a solid catalyst, wherein unsaturated carboxylic acid and alcohol are continuously fed to the reactor from an inlet thereof to form a fluid of the reaction solution in the reactor, and the vaporized organic solvent is continuously fed to the reactor from the inlet or a part near the inlet of the reactor.

9 Claims, 6 Drawing Sheets

(56) References Cited

OTHER PUBLICATIONS

International Preliminary Report on Patentability and Written Opinion dated Oct. 8, 2020 in PCT/JP2019/013011 (submitting English translation only), 7 pages.
International Search Report dated Jun. 18, 2019 in PCT/JP2019/013011 filed on Mar. 26, 2019, 2 pages.
Ohara et al., "Acrylic Acid and Derivatives", Ullmann's Encyclopedia of Industrial Chemistry $5^{th}$-Ed., 1985, vol. A1, pp. 161-176.
Zeng et al., "Design and Control of butyl acrylate reactive distillation column system", Chemical Engineering Science, vol. 61, Issue 13, 2006, pp. 4417-4431.
Reconsideration Report by Examiner before Appeal dated Jul. 5, 2023, filed in corresponding Japanese Patent Application No. 2019-059278 (w/English Language Machine Translation) 6 pages.
Reconsideration Report by Examiner before Appeal dated Jun. 26. 2023, filed in corresponding Japanese Patent Application No. 2019-059278 (w/English Language Machine Translation) 6 pages.

\* cited by examiner

METHOD FOR PRODUCING UNSATURATED CARBOXYLIC ESTER

CROSS-REFERENCE TO RELATED APPLICATION

This is a continuation of International Application PCT/JP2019/013011, filed on Mar. 26, 2019, and designated the U.S., and claims priority from Japanese Patent Application 2018-061728 which was filed on Mar. 28, 2018, the entire contents of which are incorporated herein by reference.

TECHNICAL FIELD

The present invention relates to a method for producing an unsaturated carboxylic ester using a solid catalyst in a gas-liquid mixed phase state using unsaturated carboxylic acid and alcohol as raw materials.

BACKGROUND ART

A general method for producing an unsaturated carboxylic ester is an esterification reaction using unsaturated carboxylic acid and alcohol as raw materials. In the esterification reaction, a catalyst is usually used to increase the reaction rate. The catalyst is divided into two cases: of a case in which a catalyst is dissolved in a reaction fluid (homogeneous system) when used and a case in which a catalyst is present as a solid in a reaction fluid (heterogeneous system). The heterogeneous system is further classified into a fluidized bed where a catalyst flows with a reaction fluid and a fixed bed where a catalyst is stationary and does not move. An esterification reaction performed using a fixed bed has a feature of being capable of increasing the catalyst concentration per unit space and thus easily separating the reaction fluid and the catalyst as compared with a fluidized bed or the homogeneous system.

The unsaturated carboxylic ester generated by an esterification reaction reacts with reaction by-product water, so as to be hydrolyzed into unsaturated carboxylic acid and alcohol. Hence, the reaction conversion rate reaches a level such that the esterification reaction and the hydrolysis reaction (reverse reaction) reach an equilibrium state, and cannot exceed the level.

Accordingly, reaction by-product water should be separated from the unsaturated carboxylic ester and recovered. For example, Non-Patent Literature 1 discloses a method for producing an acrylic ester, which involves feeding acrylic acid and 1.1 to 1.3 equivalents of methanol or ethanol to a fixed bed reactor packed with a cation exchange resin as a catalyst, performing an esterification reaction at 60° C. to 80° C., subsequently feeding the reaction solution to a distillation column to separate unreacted acrylic acid as a bottom liquid of the column, separating the acrylic ester, unreacted alcohol and reaction by-product water as a distillate, separating reaction by-product water via two-component separation of the distillate, separating unreacted alcohol from the separated crude acrylic ester solution by extraction and distillation, and then circulating the separated acrylic acid and alcohol to an esterification reactor.

By removing reaction by-product water, to the outside of the reaction system in the course of the esterification reaction, a hydrolysis reaction can be suppressed, and the rate of reaction conversion between unsaturated carboxylic acid such as acrylic acid and alcohol can be increased. The higher the reaction conversion rate, the less the unsaturated carboxylic acid such as unreacted acrylic acid and alcohol at the reactor outlet, so that the load of separation and recovery is reduced, and more efficient production becomes possible. Patent Literature 1 discloses a method for producing an acrylic ester, which involves feeding acrylic acid and methanol or ethanol to a reactor packed with a strongly acidic ion exchange resin, adjusting the temperature and pressure in the reactor to make the entire reaction system in a gas-liquid mixed state (bubbling state), transferring water produced as a by-product of the esterification reaction in a liquid phase to a gas phase, and thus increasing the reaction conversion rate in the liquid phase. Similarly, Patent Literature 2 discloses a method for producing an acrylic ester, which involves reacting an excessive amount of acrylic acid with alcohol having 1 to 3 carbon atoms at 60° C. to 130° C. under reduced pressure of 13 kPa to 67 kPa, thereby reducing by-products and obtaining a high reaction conversion rate. Further, Non-Patent Literature 2 discloses a method, which involves installing a reaction section having an acidic ion exchange resin in a mid-stage section of a distillation column, feeding acrylic acid from above the reaction section, feeding butanol from below the reaction section, extracting reaction by-product water from the column top, and then obtaining butyl acrylate from the column bottom. Each of these is similar to a so-called trickle bed reactor (hereinafter sometimes referred to as "TBR") in which it has a solid catalyst in the reactor and a reaction fluid is present in a mixed phase state of liquid and gas.

On the other hand, unsaturated carboxylic acid and an unsaturated carboxylic ester (hereinafter collectively referred to as "unsaturated carboxylic acids") may cause unintended polymerization due to the unsaturated bond. In particular, acrylic acid, methacrylic acid, and esters thereof (hereinafter collectively referred to as "acrylic acids") are easily polymerizable compounds that spontaneously start polymerization without the addition of a polymerization initiator. When solid matter accumulation due to unintended polymerization proceeds in a production facility, the facility is forced to shut down due to blockage or the like, so that polymerization blockage should be avoided or at least reduced. Examples of measures include distillation operation under reduced pressure for the purpose of reducing polymerizability due to a decrease in operating temperature, addition of a polymerization inhibitor for the purpose of scavenging radicals that cause polymerization, and applying of an internal structure of an apparatus having a short average stagnant time and a small number of stagnant parts for the purpose of alleviating blockage due to polymerized products. Non-Patent Literature 1 discloses methods of performing distillation of acrylic acids under reduced pressure to prevent polymerization and adding hydroquinone or phenothiazine as a polymerization inhibitor.

CITATION LIST

Patent Literature

Patent Literature 1: Japanese Patent Laid-Open No. 55-122740
Patent Literature 2: Japanese Patent Laid-Open No. 10-279523

Non-Patent Literature

Non-Patent Literature 1: Ullmann's Encyclopedia of Industrial Chemistry 5th-Ed. Vol. A1 pp. 161-176 "Acrylic Acid and Derivatives"

Non-Patent Literature 2: Chem. Eng. Sci. 61(2006) 4417-4431 "Design and control of butyl acrylate reactive distillation column system"

SUMMARY OF INVENTION

Technical Problem

In an esterification reaction, TBR, wherein a fixed bed type catalyst layer that has a high catalyst density per space and can be easily separated from a reaction fluid is used, and dehydration can be performed in parallel to increase the reaction conversion rate, is a very efficient apparatus. The reactive distillation type thereof as shown in Non-Patent Literature 2 in which a reaction solution that is a reaction fluid and a reaction gas are in countercurrent contact, is particularly excellent in that reaction by-product water can be selectively separated.

However, in the case of unsaturated carboxylic acids, it is necessary to pay attention to polymerization blockage as much as or more than the efficiency of an esterification reaction. Polymerization of unsaturated carboxylic acids in a liquid phase can be prevented by eliminating local high-temperature parts and stagnant parts and keeping the polymerization inhibitor concentration in the liquid phase above a certain level on average. Since the concentration of unsaturated carboxylic acids is low in a gas phase, polymerization does not occur substantially. However, the vapor pressure of a polymerization inhibitor used is often lower than that of unsaturated carboxylic acids, and almost no polymerization inhibitor exists in the gas phase. Unsaturated carboxylic acids condensed from the gas phase also contain no polymerization inhibitor and have high polymerizability. Therefore, it is necessary to prevent vapor condensation of unsaturated carboxylic acids by keeping the temperature of or heating the gas phase section, or to quickly add a polymerization inhibitor to the condensate.

Because of the above reasons, the inside of the distillation column where the vaporization and condensation of unsaturated carboxylic acids repeatedly take place is one of the parts where polymerization blockage tends to take place. The method described in Non-Patent Literature 2 is similar to this, and quick mixing of a condensate and a polymerization inhibitor is indispensable. However, it is extremely difficult to perform this under a condition of being packed with a solid catalyst. It is hard to say that the method is realistic because no measures are presented.

The methods disclosed in Patent Literature 1 and Patent Literature 2 employ a so-called plug flow using a tubular reactor, in which liquid and gas flow in the same direction in a tube, minimizing the frequency of vaporization and condensation of acrylic acids while sacrificing some selective separation of water, as well as equalizing the liquid and gas flow in the reactor to prevent polymerization blockage in the apparatus, and thus is considered to also have a function of quickly discharging polymerization products with relatively low molecular weights that have not been precipitated to the outside of the reactor. These methods can be said as more realistic methods in terms of measures against polymerization blockage.

A high reaction conversion rate in an esterification reaction in TBR is considered to be based on separation from a liquid phase due to rapid vaporization of reaction by-product water. Water vaporization requires heat of vaporization, and in the case of the tubular reactor, heat of vaporization is supplied to a reaction fluid in a tube through the inner wall surface of the reaction tube. This is similar to a case of using a multi-tubular heat exchanger as a reboiler of a distillation column.

However, compared to such a multi-tubular heat exchanger, in which a reaction fluid consisting entirely or mostly of a liquid flows in the tube at a linear velocity of 0.3 to 3 m/sec, in a tubular reactor wherein a gas-liquid multi-phase flow containing the gas larger in volume ratio than the liquid flows in a tube packed with a solid catalyst at a linear velocity of less than 0.3 m/second, the stagnancy of the local reaction fluid on the inner wall surface of the tube and the possibility of the accompanying polymerization blockage are greatly increased. Increasing the in-tube linear velocity of the reaction fluid to the same level as that of a reboiler is not practical because the stagnant time required for the reaction cannot be kept and the increase in the differential pressure due to the packed catalyst will be extremely high. By reducing the temperature difference ($\Delta T$) between the reaction fluid flowing inside the tube and the heat medium fluid flowing outside the tube, local overheating can be alleviated and polymerization blockage can be reduced. However, it is necessary to increase the surface area (heat transfer area) in the reaction tube for supplying heat amount required in inverse proportion to $\Delta T$. Extending the reaction tube length in order to increase the heat transfer area is not preferable because it increases the reactor capacity and impairs the efficient esterification reaction which is an advantage of TBR. If the reaction tube is made thinner, the heat transfer area can be increased in inverse proportion to the diameter of the tube, but the number of reaction tubes increases, which not only increases the production cost of the reactor, but also increases the workload involved upon packing of the reaction tube with a catalyst. Further, another problem is such that the thinner the reaction tube, the more difficult the recovery work when polymerization blockage occurs in the reaction tube.

Objects of the present invention are to solve the above-mentioned conventional problems, and to provide a method for producing an unsaturated carboxylic ester, wherein in an esterification reaction of unsaturated carboxylic acid, the risk of polymerization blockage is lowered while maintaining a high conversion rate, and the required equipment cost and the workload involved are kept low.

Solution to Problem

As a result of repeated studies to solve the above-mentioned problems, the present inventors have discovered that a high reaction conversion rate can be obtained without substantially supplying heat to a reactor by using a reactor packed with a solid catalyst in an esterification reaction of unsaturated carboxylic acid, feeding raw-material unsaturated carboxylic acid and alcohol to the reactor, and feeding a vaporized organic solvent in a concurrent flow.

The present invention has been achieved based on such findings, and is summarized as follows.

[1] A method for producing an unsaturated carboxylic ester by an esterification reaction of unsaturated carboxylic acid and alcohol using a reactor packed with a solid catalyst, comprising:
a step of continuously feeding unsaturated carboxylic acid and alcohol to the reactor from an inlet of the reactor to form a fluid of the reaction solution within the reactor; and
a step of continuously feeding a vaporized organic solvent into the reactor from the inlet of or a part near the inlet of the reactor.

[2] The method for producing an unsaturated carboxylic ester according to [1], wherein the organic solvent is an aliphatic hydrocarbon or an aromatic hydrocarbon.

[3] The method for producing an unsaturated carboxylic ester according to [1] or [2], wherein the boiling point of the organic solvent under atmospheric pressure is lower than the boiling point of the unsaturated carboxylic acid under atmospheric pressure.

[4] The method for producing an unsaturated carboxylic ester according to any one of [1] to [3], wherein the organic solvent is toluene.

[5] The method for producing an unsaturated carboxylic ester according to any one of [1] to [4], wherein the reactor is a vertical reactor and the fluid of the reaction solution is downflow.

[6] The method for producing an unsaturated carboxylic ester according to any one of [1] to [5], comprising: a step of separating an esterification reactant discharged from the reactor into a liquid phase and a gas phase;
a step of continuously feeding the liquid phase to a reactor (A) separately installed downstream of the reactor from an inlet of the reactor (A), so as to form a fluid of the reaction solution within the reactor (A); and
a step of recovering a gaseous organic solvent from the gas phase, and then continuously feeding the recovered gaseous organic solvent to the reactor (A) from the inlet of or a part near the inlet of the reactor (A).

[7] The method for producing an unsaturated carboxylic ester according to any one of [1] to [6], comprising:
a step of separating an esterification reactant discharged from the reactor into a liquid phase and a gas phase;
a step of purifying the separated liquid phase to obtain an unsaturated carboxylic ester; and
a step of recovering a gaseous organic solvent from the separated gas phase, and then continuously feeding the recovered gaseous organic solvent to the reactor from the inlet of or a part near the inlet of the reactor.

[8] A method for producing an unsaturated carboxylic ester by an esterification reaction of unsaturated carboxylic acid and alcohol using a reactor packed with a solid catalyst, comprising
a step of continuously feeding a vaporized organic solvent to the reactor from the inlet of or a part near the inlet of the reactor; and
a step of continuously feeding unsaturated carboxylic acid and alcohol to the reactor from the inlet of the reactor, after the internal pressure of the reactor is kept within the range of predetermined pressure ±5% for at least 30 minutes.

[9] The method for producing an unsaturated carboxylic ester according to [8], comprising a step of continuously feeding the unsaturated carboxylic acid and the alcohol to the reactor from the inlet of the reactor after the fluctuation width of the internal temperature of the reactor is kept at 0.5° C. or lower for at least 30 minutes.

Advantageous Effects of Invention

According to the present invention, an unsaturated carboxylic ester can be produced at a high conversion rate while reducing the polymerization risk of a reactor and keeping the workload involved low in an esterification reaction.

DESCRIPTION OF EMBODIMENTS

Hereinafter, the method of the present invention will be described in detail with reference to the drawings. However, the present invention is not limited to the following description, and various modifications may be made within the scope of the present invention.

Figure 1:
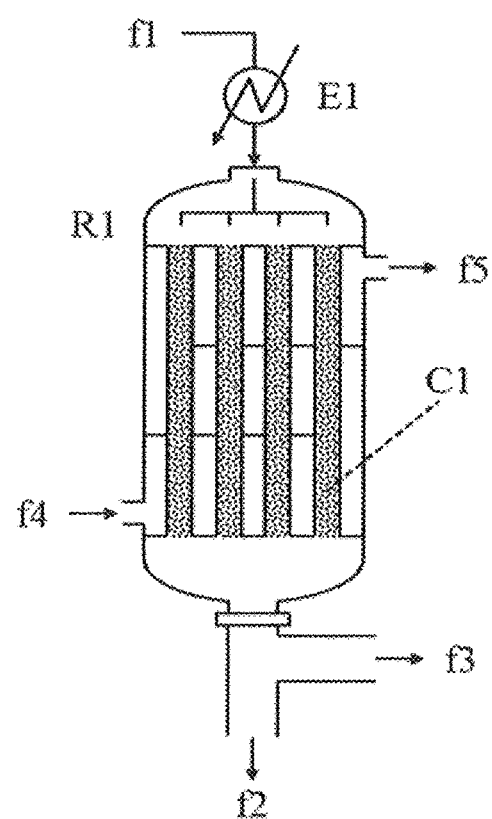
FIG. 1 is a schematic diagram showing an example of a reactor for conventional production of an unsaturated carboxylic ester.

FIG. 1 is a schematic diagram showing an example of a reactor for conventional production of an unsaturated carboxylic ester. In the following description, an embodiment using acrylic acid as unsaturated carboxylic acid will be mainly described. This is because, among unsaturated carboxylic acids, acrylic acid has high polymerizability, and receives many benefits from reduction of the polymerization risk of the reactor, which is one of the features of the present invention. However, similar effects can be obtained from the use of methacrylic acid etc., which are other unsaturated carboxylic acids.

A feed liquid (f1) containing raw-material acrylic acid, alcohol, a polymerization inhibitor, an acrylic ester circulated from downstream steps, and, if necessary, a solvent, etc., is heated to near the reaction temperature by a heater (E1), and then continuously fed to a multi-tubular reactor (R1) packed with a solid catalyst (C1). The multi-tubular reactor (R1) is fed with a heat medium (f4) that circulates around the outer periphery of each reaction tube, and the heat medium (f4) is discharged from the reactor (R1), thereby controlling the temperature within the reactor. The pressure is adjusted so that the inside of the reactor is in a gas-liquid mixed phase state, and the reaction fluid at the reactor outlet is separated into a liquid flow (f2) and a gas flow (f3).

Figure 2:
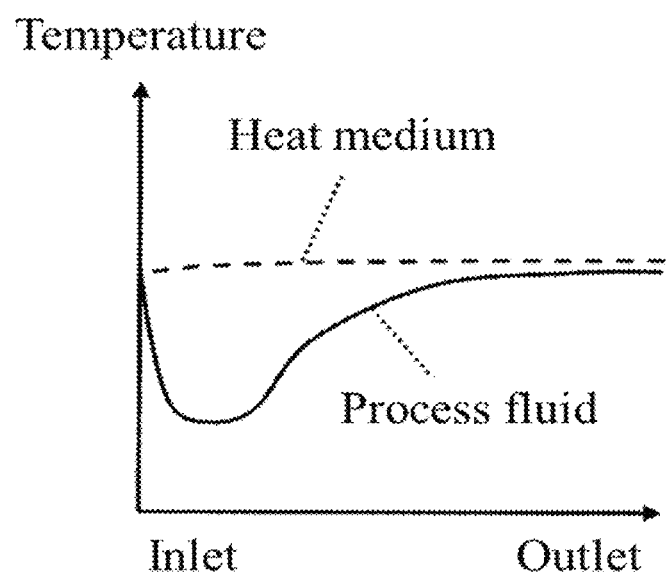
FIG. 2 is a conceptual diagram of the temperature distribution in a reactor for conventional production of an unsaturated carboxylic ester.

FIG. 2 is a conceptual diagram of the temperature distribution in the multi-tubular reactor (R1) of FIG. 1. The closer it gets to the inlet side of the multi-tubular reactor, the higher the raw material concentration.

Accordingly, the amount of by-product water accompanying an esterification reaction increases. The by-product water vaporizes while removing heat of vaporization from the reaction fluid, so that its temperature decreases. For example, when 2-ethylhexyl acrylate is produced from acrylic acid and 2-ethylhexanol, the temperature of the reaction fluid is reduced by about 1° C. to vaporize water generated at a reaction conversion rate of 1%. Heat is supplied from the heat medium circulating outside the reaction tube to the reaction fluid. However, the amount of heat transfer is proportional to the temperature difference between the heat medium and the reaction fluid. Hence, the temperature of the reaction fluid decreases once, then starts to increase, and thus reaches around the temperature of the heat medium at the outlet of the multi-tubular reactor. In order to vaporize reaction by-product water while maintaining the reaction temperature necessary for the esterification reaction, a multi-tubular reactor having a large heat transfer area for the reaction fluid is essential in commercial production.

It is possible to omit the heater (E1) and supply all the necessary heat amount by the multi-tubular reactor (R1). However, as heat amount supplied in the multi-tubular reactor (R1) increases, the size of the multi-tubular reactor (R1) is increased. Hence, the economic efficiency decreases. Adding a solvent not involved in an esterification reaction and increasing the proportion of matter to be circulated from downstream steps to the multi-tubular reactor increase the amount of liquid to be fed to the multi-tubular reactor, thereby lowering the temperature decrease width of the reaction fluid inversely proportional to the amount of liquid fed. However, this is not an essential solution for the temperature decrease.

Figure 3:
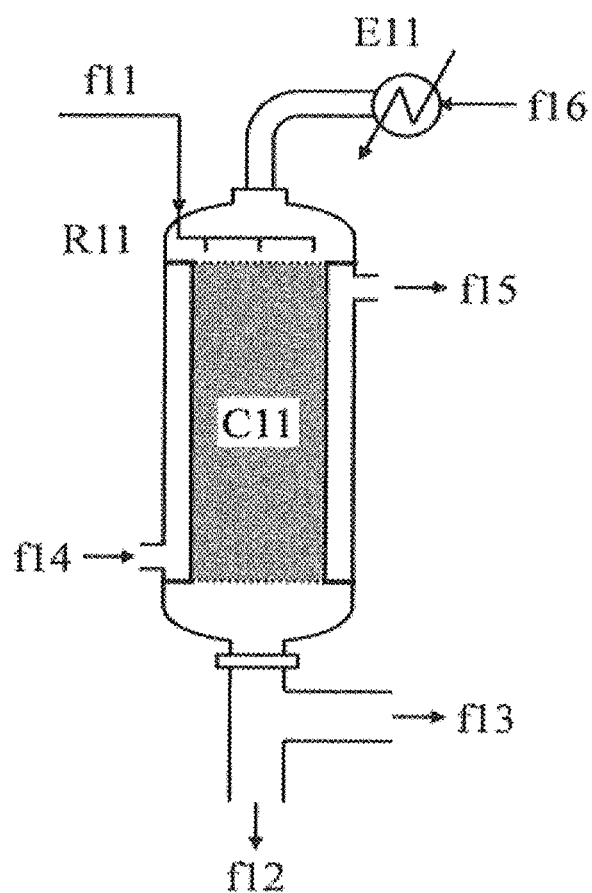
FIG. 3 is a schematic diagram showing an example of a reactor for the production of an unsaturated carboxylic ester according to the present invention.

FIG. 3 is a schematic diagram showing an example of a reactor for the production of an unsaturated carboxylic ester of the present invention. This reactor includes an inlet section, a reaction section containing a solid catalyst, and an outlet section from the upper part in the figure. A feed liquid (f11) containing raw-material acrylic acid, alcohol, a polymerization inhibitor, and an acrylic ester etc., circulated from downstream steps is continuously fed to the inlet section of the reactor (R11). For feeding the feed liquid (f11), a shower nozzle or an atomizing nozzle is used so as to uniformly distribute the feed liquid over the cross section of the reactor (R11), but is not limited thereto. The feed liquid (f11) fed to the reactor (R11) exists as a fluid of the reaction solution in the reactor, and can be esterified by contacting with a vaporized organic solvent (f16) described later.

Separately, the organic solvent (f16) is vaporized by a vaporizer (E11) and then continuously fed to the inlet section of the reactor (R11). The organic solvent (f16) is not necessarily fed to the inlet section of the reactor, and may be continuously fed to a part near the inlet section; that is, onto the side of the inlet section of the reaction section. Specifically, "a part near (the inlet)" may be the ½ part, the ⅓ part, the ¼ part, or the ⅕ part, which is located closest to the side of the inlet section, of the solid catalyst (C11) in the vertical direction of the solid catalyst (C11) in the figure.

The reactor (R11) is a jacket type reactor having a vessel packed with the solid catalyst (C11) and a path through which the heat medium (f14) flows in the outer peripheral part, and thus is a downflow reactor in which the fluid moves in the vertical direction.

A packed bed having no catalytic activity may be provided on the packed solid catalyst (C11) for the purpose of more uniform diffusion of the feed liquid (f11) and preheating with a vaporized organic solvent. The type thereof is not particularly limited, for example, it may be a metal random packing because of its high porosity, low pressure drop, and high thermal conductivity, etc. Since polymers of acrylic acids are not easily deposited, it may be a random packing made of a fluorine resin such as polytetrafluoroethylene, and is preferably a random packing or a wire mesh surface-processed with the fluorine resin, and a wire mesh is more preferred from the viewpoint of easy handling at the time of attachment/detachment.

Unlike the multi-tubular reactor (R1) that actively supplies heat from a heat medium to a reaction fluid, the heat medium in the reactor (R11) is intended to prevent heat dissipation from the reaction fluid to the outside air, and thus does not require a large heat amount. Therefore, instead of introducing the heat medium into the reactor (R11), a heating means such as an electric heater or steam tracing can also be used. In addition, in order to prevent the solid catalyst and the reaction fluid in the reactor (R11) vessel from being overheated locally, a heat insulating material or the like is preferably disposed between an electric heater or a steam trace piping and the outer wall surface of the vessel, so as to avoid direct contact between them.

The reaction fluid is a mixed fluid in a reactor, which contains, in addition to a feed liquid (f11) and the organic solvent (f16), an unsaturated carboxylic ester such as an acrylic ester as a reaction product, and reaction by-product water, wherein both liquid and gas can be present therein.

The solid catalyst (C11) to be used is not particularly limited, and a general catalyst that can be used for an esterification reaction of unsaturated carboxylic acid and alcohol can be used. The smaller the particle size, the larger the surface area of the catalyst per unit space, and the esterification reaction can be carried out more efficiently, but the average particle size is preferably 0.1 mm or more and more preferably 0.2 mm or more so that the pressure drop associated with gas flow is not too large.

As the solid catalyst, a porous ion exchange resin is preferable because the catalyst concentration per unit space is high and the particle size distribution is narrow. An activated clay obtained by thermal oxidation treatment of acidic clay such as montmorillonite is preferred in terms of physical strength and price. When the scale of an ester production plant is large and the operation period is as long as 3 months to several years, the porous ion exchange resin is excellent in economic efficiency. In contrast, when the plant scale is small, the operation period is as short as one week to several months, and the renewal frequency of a catalyst associated with the change of the manufacturing items is high, the activated clay is excellent in terms of economy and workload involved.

Water produced as a by-product of an esterification reaction is vaporized by exchanging heat with the vapor of an organic solvent, and the organic solvent subjected to the heat exchange is condensed. When the composition of the azeotropic mixture of water and the organic solvent is A (water): B (organic solvent) (molar ratio), the gasified organic solvent (hereinafter may also be referred to as "organic solvent vapor") gasified to an amount that is B/A molar fold relative to the reaction by-product water is the minimum required amount. However, since all of the fed organic solvent vapor cannot perform heat exchange with the reaction by-product water. Hence, the feed amount of the organic solvent vapor is required to be at least 1.2 times and preferably 1.3 times or more the minimum required amount.

As the amount of an organic solvent vapor to be fed increases, the vaporization of reaction by-product water proceeds more rapidly. However, in view of increases in heat amount required for vaporization of the organic solvent and the load required for separation and recovery of the organic solvent in downstream steps, the feed amount of the organic solvent vapor is preferably 5 times or less, and more preferably 3 times or less the minimum required amount.

The organic solvent to be used is preferably an aliphatic hydrocarbon or an aromatic hydrocarbon that can be easily separated and recovered for reuse and has high chemical stability. If the boiling point of the organic solvent is too low, heat exchange with reaction by-product water is difficult to proceed, which is not economical. In contrast, if the boiling point is too high, heat exchange with also unreacted acrylic acid takes place in the process liquid to vaporize acrylic acid, so that the polymerization blockage derived from the vaporized acrylic acid is likely to occur. Furthermore, since no esterification reaction proceeds in a gas phase, the reaction conversion rate of acrylic acid may be lowered. In view of these, the boiling point of the organic solvent is preferably lower than the boiling point of acrylic acid, and ranges from more preferably 70° C. to 130° C., and further preferably 80° C. to 120° C.

The temperature of the reaction fluid is controlled by the pressure in the reactor. Since the composition of the reaction fluid continuously changes along the reaction axis and a pressure drop associated with the flow of the reaction fluid takes place, it is difficult to equalize the temperatures in all reaction zones. Examples of a method for controlling the operation of the reactor include a method of measuring the temperature in the reactor at a plurality of points along the reaction axis and adjusting the pressure in the reactor so that the temperatures at specific positions are constant, a method of maintaining the temperatures at specific positions in the reactor at a level by maintaining the pressure in the reactor at a level and adjusting the amount and the temperature of the organic solvent vapor generated by the vaporizer (E11), and a method of maintaining the pressure in the reactor and the amount and the temperature of the fed vapor at a level, and allowing a slight temperature fluctuation in the reactor.

A higher reaction temperature is preferred, since it results in a higher reaction rate. However, an excessive temperature increase should be avoided because the polymerization reaction and the blockage associated therewith easily take place. The appropriate reaction temperature varies depending on the type of an ester, but is generally in the range of 60° C. to 120° C., preferably in the range of 70° C. to 110° C.

The reaction pressure depends on the type of an organic solvent to be used, but is 0.2 to 1.0 times the vapor pressure of water at the reaction temperature, which is an average criterium. The reaction fluid at the outlet of the reactor is separated into a liquid flow (f12) mainly composed of an acrylic ester and a gas flow (f13) mainly composed of an organic solvent and reaction by-product water.

When an unsaturated carboxylic ester is produced using the reactor of the embodiment, the timing for feeding a raw material containing unsaturated carboxylic acid and alcohol and a vaporized organic solvent to the reactor is not particularly limited. In one embodiment, the vaporized organic solvent is continuously fed to the reactor. After the internal pressure of the reactor is kept within the range of predetermined pressure ±5%, preferably within the range of predetermined pressure ±3%, more preferably within the range of predetermined pressure ±2% for at least 30 minutes, preferably for 45 minutes or more, and more preferably for 60 minutes or more, unsaturated carboxylic acid and alcohol may be continuously fed to the reactor from the reactor inlet.

In another embodiment, the vaporized organic solvent is continuously fed to the reactor. After the fluctuation width of the internal temperature of the reactor is kept at 0.5° C. or lower, preferably 0.4° C. or lower, more preferably 0.3° C. or lower for at least 30 minutes, preferably for 45 minutes or more, more preferably 60 minutes or more, the unsaturated carboxylic acid and alcohol may be continuously fed to the reactor from the reactor inlet.

Note that the internal temperature of the reactor may be the temperature of the catalyst layer. Moreover, the internal pressure of the reactor may be, for example, the pressure at the inlet section or the outlet section.

In this embodiment, reaction by-product water moves from a liquid phase to a gas phase in a reaction fluid because of heat exchange with organic solvent vapor. However, since the liquid flow and the gas flow are concurrent, reaction by-product water is also present in an equimolar amount of the generated acrylic ester at the reactor outlet. Most of the water molecules are present in the gas phase, but some of them are present in the liquid phase due to vapor-liquid equilibrium, which hinders improvement of the reaction conversion rate. An example of a measure for improvement is a method that involves performing the feeding of organic solvent vapor and the separation of reaction by-product water in multi-stages.

Figure 4:
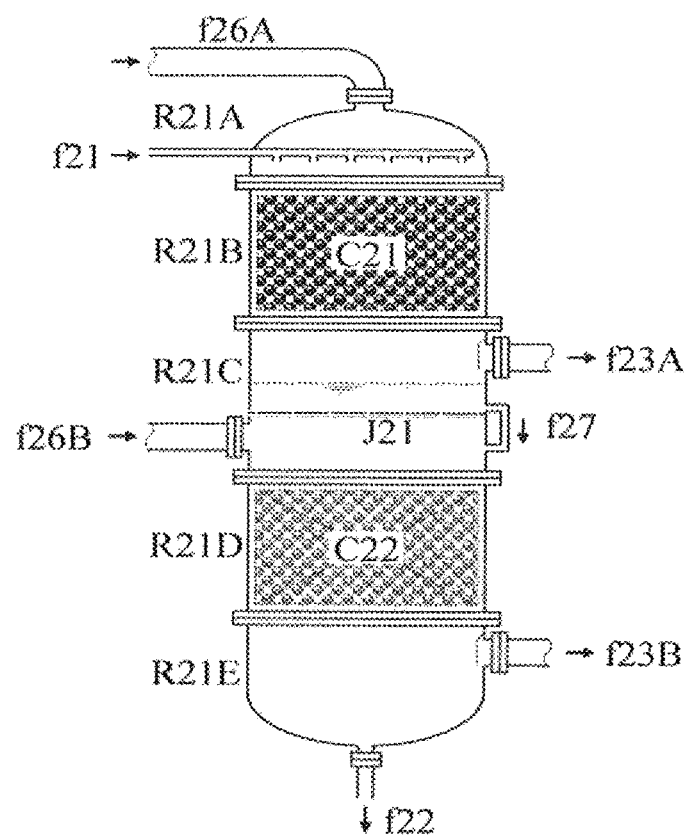
FIG. 4 is a schematic diagram showing another example of a reactor for the production of an unsaturated carboxylic ester according to the present invention.

FIG. 4 is a schematic diagram showing another example of a reactor for producing an unsaturated carboxylic ester, which is produced by applying the reactor shown in FIG. 3 to a serial two-stage reactor. A feed liquid (f21) containing raw-material acrylic acid, alcohol, a polymerization inhibitor, an acrylic ester circulated from downstream steps, etc., and organic solvent vapor (f26A) are fed to an upper frange section (R21A) of the reactor, and then an esterification reaction is performed with a solid catalyst (C21) of a first-stage reaction section (R21B). Thereafter, a gas flow (f23A) consisting of an organic solvent and reaction by-product water is extracted from the side surface at an intermediate connection section (R21C) of the reactor, and a liquid flow containing an acrylic ester, an unreacted raw material, a condensed organic solvent, and the like (hereinafter also referred to as a process liquid) falls through a plate hole while forming a liquid depth on a perforated plate (J21) installed below.

In the intermediate connection section (R21C), organic solvent vapor (f26B) is newly fed from the side surface downstream of the perforated plate (J21). Due to the liquid depth formed on the perforated plate (J21), the additionally fed organic solvent vapor (f26B) is fed to a second-stage reaction section (R21D) together with the process liquid without flowing into the first-stage reaction section (R21B) or a gas flow extraction piping (f23A).

As a measure for preventing the inflow of the organic solvent vapor (f26B), a tube trap such as an S trap can also be used instead of the perforated plate (J21). However, the perforated plate is more preferable in that the use of such a trap creates a stagnant part of acrylic acids in the trap, requires a distributor to disperse the process liquid at the trap outlet throughout the second-stage reaction section (R21D), and so on.

The process fluid that has finished the reaction with the solid catalyst (C22) is separated into a gas flow (f23B) mainly composed of an uncondensed organic solvent and reaction by-product water, and a liquid flow (f22) mainly composed of an acrylic ester and a condensed organic solvent at the lower frange section (R21E) of the reactor.

The gas flow (f23A) containing the organic solvent extracted at the intermediate connection section (R21C) of the reactor is condensed and then separated into an aqueous layer and a solvent layer in a storage tank (not shown). The organic solvent recovered from the solvent layer may be vaporized again and then fed to the inlet section of the second-stage reactor as organic solvent vapor (f26B). In this embodiment, the intermediate connection section (R21C) constitutes the outlet section of the first-stage reactor and the inlet section of the second-stage reactor.

FIG. 4 shows an example of a serial two-stage reactor, but the reactor to be used herein is not limited thereto, and can be a multi-stage system. Since reaction by-product water can be sequentially extracted, it is preferable that the number of stages is large. However, in view of the fact that the structure of the instrument is complicated, and the required equipment cost is increased, resulting in nonconformity to the purpose of the present invention, 2 to 5 stages are preferable.

The multiple reactors in FIG. 3 can also be connected in series. In this case, multiple reactors can also be stacked in the vertical direction, but from the viewpoint of construction and maintenance, multiple reactors are preferably disposed at the same height, and the reaction solution obtained from the bottom of each reactor is preferably sent to the upper part of the next reactor via a liquid feed pump. Since high discharge pressure can be obtained by the liquid feed pump, a shower nozzle or a spray nozzle can be used for uniform dispersion of the feed liquid even in the second and subsequent-stage reactors.

In such embodiments of multi-stage reactors or multiple reactors connected in series, an organic solvent recovered from the fluid after the reaction may also be used as an organic solvent for the reaction together with the reaction raw material, and may be circulated to the upstream reactor(s) and then further fed to the downstream reactor(s).

Figure 5:
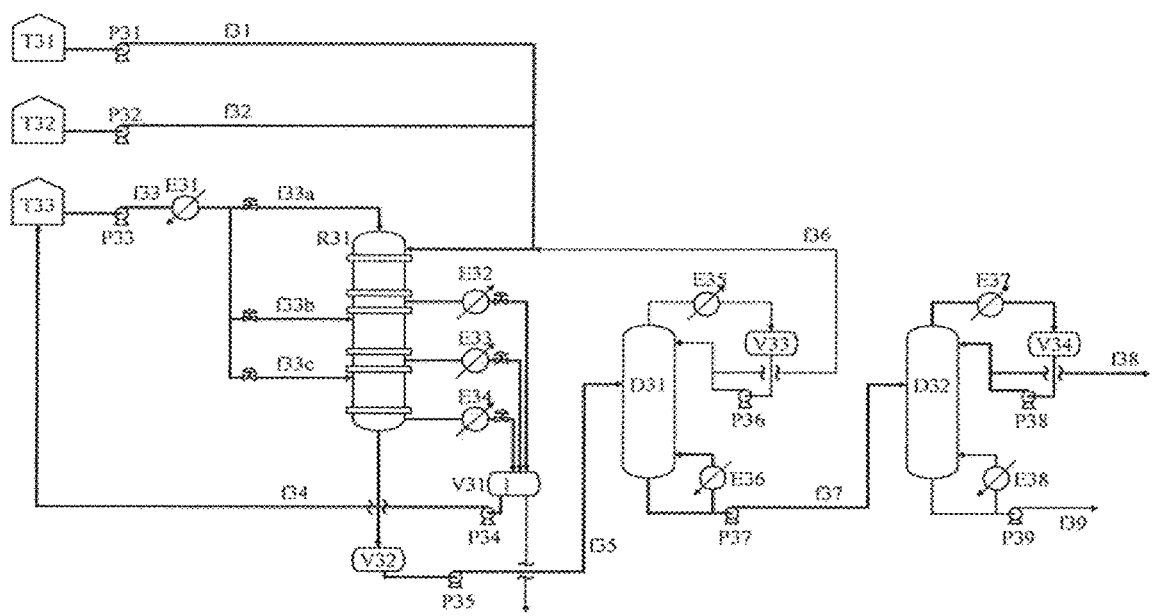
FIG. 5 is a schematic diagram showing an example of the process, including a reactor for the production of an unsaturated carboxylic ester according to the present invention.

FIG. 5 is a schematic diagram showing an example of a process for producing an unsaturated carboxylic ester. After acrylic acid and alcohol are fed from raw-material tanks (T31, T32) to a three-stage reactor (R31) and then an organic solvent is sent from a tank (T33) to a vaporizer (E31) to be organic solvent vapor, the organic solvent vapor is divided into three portions and fed to the three-stage reactor (R31). The organic solvent and reaction by-product water vapor separated from each stage are condensed in condensers (E32 to E34), and then separated into an aqueous layer and a solvent layer in a storage vessel (V31). The aqueous layer is extracted out of the system as waste water, and the solvent layer is circulated to the tank (T33).

The reaction fluid obtained from the bottom section of the three-stage reactor (R31) is once collected in the storage vessel (V32) and then sent to a light boiling separation distillation column (D31). A stream mainly composed of an organic solvent, raw-material alcohol, raw-material acrylic acid and the like is obtained from the column top of the light boiling separation distillation column (D31), and is circulated to the three-stage reactor (R31). Unlike this, a column top distillate stream mainly composed of an organic solvent and a side-cut stream mainly composed of raw-material alcohol and the like are obtained by side-cutting from the rectifying section other than the column top of the light boiling separation distillation column (D31). The column top distillate stream can also be circulated to the tank (T33) and the side cut stream can also be circulated to the three-stage reactor (R31) (not shown). A stream mainly composed of an acrylic ester obtained from the column bottom of the light boiling separation distillation column (D31) is sent to a purification distillation column (D32), and then a purified acrylic ester is obtained from the column top. In addition, a distillation column and an extraction device can be arbitrarily added for purification and recovery of valuable materials.

Figure 6:
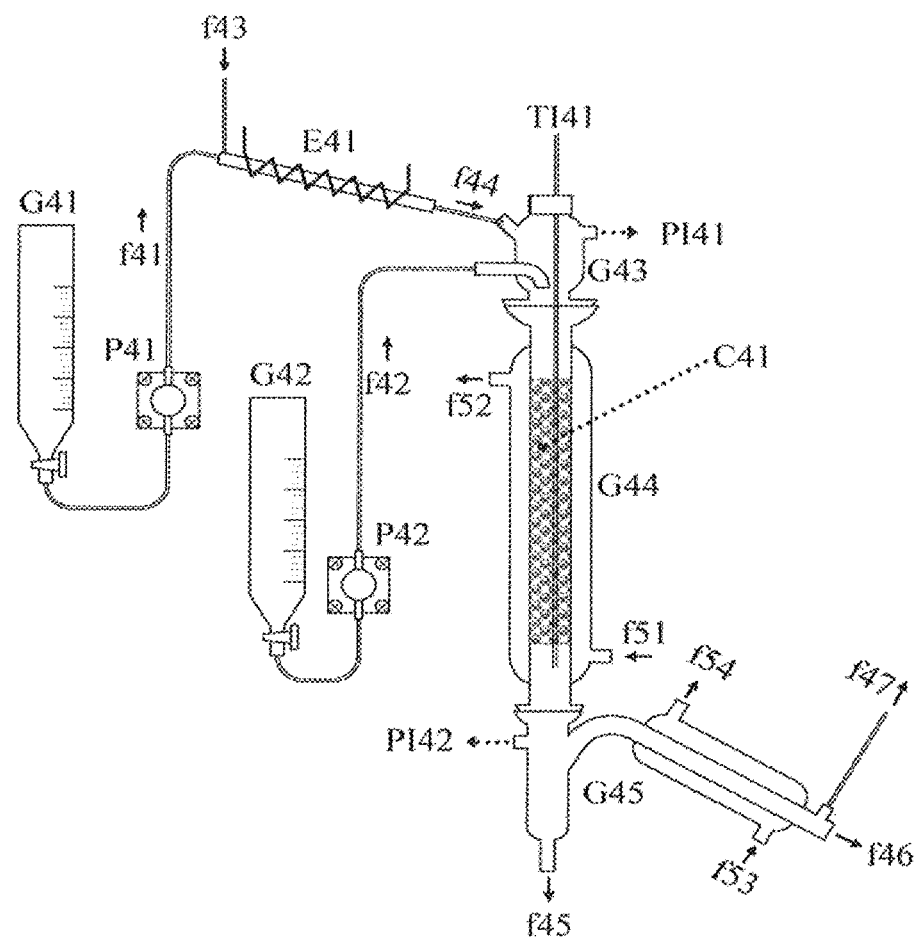
FIG. 6 is a schematic diagram of an experimental apparatus for the production of an unsaturated carboxylic ester according to the present invention.

FIG. 6 is a schematic diagram of an experimental apparatus for producing an unsaturated carboxylic ester. The apparatus comprises a solvent container (G41), a solvent feed pump (P41), a solvent vaporizer (E41), a container for a mixed solution of acrylic acid, alcohol and a polymerization inhibitor (G42), a mixed solution feed pump (P42), an inlet-section glass apparatus (G43) of a reaction device, the reaction-section glass apparatus (G44) to be packed with a solid catalyst, an outlet-section glass apparatus (G45) for performing gas-liquid separation of a reaction fluid and condensation of the separated gas, and a plurality of thermocouples (TI41) bundled for measurement of temperature in the reaction device. The reaction-section glass apparatus (G44) is a jacket-type double tube, and a high-temperature heat medium (f51) is passed through the jacket section. Cold water (f53) is passed through the cooling section of the outlet-section glass apparatus (G45). The process liquid (f45) consisting of the generated ester and condensed solvent is collected in a receiver (not shown), and the gas condensate (f46) consisting of uncondensed solvent and reaction by-product water is also collected in a different receiver (not shown). Nozzles (PI41, PI42) installed in the inlet-section glass apparatus (G43) and the outlet-section glass apparatus (G45) are connected to a pressure gauge and controlled by a pressure valve (not shown) at a portion beyond a vacuum line (f47). A small amount of nitrogen is fed from (f43) in order to replace with nitrogen in the system at the start of operation and to avoid an explosion composition in the vacuum system when the operation is continued.

Example 1

(Dehydration of Solid Catalyst)

PK216 (H type, Mitsubishi Chemical Corporation), which is a porous strong acid ion exchange resin, was used as a solid catalyst. After the resin was immersed in tetrahydrofuran, it was packed in a glass column and toluene was passed through the column to remove the contained water.

An esterification reaction was performed using the apparatus of FIG. 6. The reaction-section glass apparatus (G44) (inner diameter: 2 cm) was packed with 60 cm$^3$ of the dehydrated porous strong acid ion exchange resin, and the pressure in the inlet-section glass apparatus (G43) was adjusted to 50 kPa. The total amount of toluene added to a solvent container (G41) was vaporized at a rate of 34.8 g/hour with a solvent vaporizer (E41) and then fed to the inlet-section glass apparatus (G43). The heat medium for external circulation was set at 99° C. Cold water at 5° C. was circulated in a gas cooling section. The operation was continued for 2 hours until the temperature in the catalyst layer became constant and no water was contained in the condensate. The internal pressure in the apparatus (G44) was kept within the range of predetermined pressure ±1% for at least 60 minutes, and the fluctuation width of the internal temperature was 0.3° C. or lower.

While maintaining the reaction pressure and the flow rate of toluene, next, a mixed solution of acrylic acid, 2-ethylhexanol in an equimolar amount of the acrylic acid, and 300 wt ppm of hydroquinone as a polymerization inhibitor was added to a mixed solution container (G42) and then feeding was started. The temperature in the catalyst layer was quickly stabilized at 93° C. to 94° C. at both the inlet and the outlet, and the composition at the reactor outlet reached a steady state within about 2 hours from the start of feeding raw materials. The experiment was continued for a maximum of 6 hours, but no difference was found in the reaction conversion rate. The results are shown in the following table.

TABLE 1

|  | Feed flow rate to reactor (g/hour) | Liquid flow rate at reactor outlet (g/hour) | Gas flow rate at reactor outlet (g/hour) |
| --- | --- | --- | --- |
| Toluene | 34.8 | 9.4 | 25.4 |
| Acrylic acid | 6.6 | 0.6 | 0.7 |
| 2-ethylhexanol | 11.3 | 1.5 | 0.3 |
| 2-ethylhexyl acrylate | — | 11.6 | 1.2 |
| Water | — | 0.1 | 1.2 |
| High boiling point substance | — | 0.7 | — |

The reaction conversion rate of acrylic acid was 80.0%.

Through repetition of the same experiment, the temperature in the catalyst layer was confirmed by changing the position of the thermocouple, but the temperature in the layer was almost constant.

Example 2

An esterification reaction was performed in the same manner as in Example 1, except that the pressure in the inlet-section glass apparatus (G43) was adjusted to 40 kPa. The temperature in the catalyst layer was constant at about 85° C., and the reaction conversion rate of acrylic acid was 74.8%.

Comparative Example 1

An esterification reaction was performed in the same manner as in Example 1, except that the pressure in the inlet-section glass apparatus (G43) was increased to about 65 kPa after dehydration of an ion exchange resin by toluene vapor flow, so as to feed solvent toluene in the form of droplets at 90° C. to 95° C. It was confirmed visually that the inside of the catalyst layer was a gas-liquid mixed layer flow, but the reaction conversion rate was less than 50%. Although the temperature of the inlet section and that of the outlet section of the catalyst layer were about 93° C., portions at less than 60° C. were confirmed on the inlet side when the temperature was confirmed by moving the thermocouple.

Comparative Example 2

In the same manner as in Example 1, dehydration of the ion exchange resin by toluene vapor flow, and subsequent feeding of raw-material acrylic acid, 2-ethylhexanol in an equimolar amount of the raw-material acrylic acid and hydroquinone were performed. The raw materials were continuously fed for 2 hours to perform an esterification reaction. The reaction conversion rate of acrylic acid at this time was 80.4°.

Next, the esterification reaction was continued while maintaining the pressure in the inlet-section glass apparatus (G43) at 50 kPa, and the toluene flow rate of the solvent feed pump (P41) was gradually reduced to zero, which required 1 hour. An increase in the liquid ratio in the catalyst layer was confirmed by visual observation. Since the amount of liquid retained in the catalyst layer changed, the flow rate at the reactor outlet was not stabilized before it approached to a level near the steady state, and the reaction conversion rate could not be calculated. Four hours after the amount of toluene fed was reduced to zero, the rate of toluene discharged from the reactor outlet was less than 0.3 g/hour, and the reaction conversion rate of acrylic acid decreased to about 35%.

REFERENCE SIGNS LIST

C1, C11, C21, C22, C41 Solid catalyst
D31 Light boiling separation distillation column
D32 Purification distillation column
E1 Heater
E11, E31 Vaporizer
E32-35, E37 Condenser
E36, E38 Reboiler
E41 Solvent vaporizer
G41 Solvent container
G42 Mixed solution container
G43 Inlet-section glass apparatus
G44 Reaction-section glass apparatus
G45 Outlet-section glass apparatus
J21 Perforated plate
P31 to P39 Liquid feed pump
P41 Solvent feed pump
P42 Mixed solution feed pump
PI41, PI42 Nozzle
R1 Multi-tubular reactor
R11 Reactor
R21A Upper frange section
R21B First-stage reaction section
R21C Intermediate connection section
R21D Second-stage reaction section
R21E Lower frange section
R31 Three-stage reactor
T31, T32, T33 Tank
TI41 Thermocouple
V31-V34 Storage vessel
f1, f11, f21 Feed liquid
f2, f12, f22 Liquid flow
f3, f13, f23B Gas flow
f4, f14, f51 Heat medium
f16 Organic solvent
f26A, f26B Organic solvent vapor
f23A Gas flow consisting of organic solvent and reaction by-product water
f43 Nitrogen
f45 Process liquid
f46 Condensate
f47 Vacuum line
f53 Cold water

What is claimed is:

1. A method for producing an unsaturated carboxylic ester by an esterification reaction of unsaturated carboxylic acid and alcohol using a reactor packed with a solid catalyst, comprising:
   a step of continuously feeding unsaturated carboxylic acid and alcohol to the reactor from an inlet of the reactor to form a fluid of the reaction solution within the reactor; and
   a step of continuously feeding a vaporized organic solvent into the reactor from the inlet of or a part near the inlet of the reactor.

2. The method for producing an unsaturated carboxylic ester according to claim 1, wherein the organic solvent is an aliphatic hydrocarbon or an aromatic hydrocarbon.

3. The method for producing an unsaturated carboxylic ester according to claim 1, wherein the boiling point of the organic solvent under atmospheric pressure is lower than the boiling point of the unsaturated carboxylic acid under atmospheric pressure.

4. The method for producing an unsaturated carboxylic ester according to claim 1, wherein the organic solvent is toluene.

5. The method for producing an unsaturated carboxylic ester according to claim 1, wherein the reactor is a vertical reactor and the fluid of the reaction solution is downflow.

6. The method for producing an unsaturated carboxylic ester according to claim 1, further comprising:
   a step of separating an esterification reactant discharged from the reactor into a liquid phase and a gas phase;
   a step of continuously feeding the liquid phase to a reactor (A) separately installed downstream of the reactor from an inlet of the reactor (A), so as to form a fluid of the reaction solution within the reactor (A); and a step of recovering a gaseous organic solvent from the gas phase, and then continuously feeding the recovered gaseous organic solvent to the reactor (A) from the inlet of or a part near the inlet of the reactor (A).

7. The method for producing an unsaturated carboxylic ester according to claim 1, further comprising:
   a step of separating an esterification reactant discharged from the reactor into a liquid phase and a gas phase;
   a step of purifying the separated liquid phase to obtain an unsaturated carboxylic ester; and
   a step of recovering a gaseous organic solvent from the separated gas phase, and then continuously feeding the recovered gaseous organic solvent to the reactor from the inlet of or a part near the inlet of the reactor.

8. A method for producing an unsaturated carboxylic ester by an esterification reaction of unsaturated carboxylic acid and alcohol using a reactor packed with a solid catalyst, comprising
   a step of continuously feeding a vaporized organic solvent to the reactor from the inlet of or a part near the inlet of the reactor; and
   a step of continuously feeding unsaturated carboxylic acid and alcohol to the reactor from the inlet of the reactor, after the internal pressure of the reactor is kept within the range of predetermined pressure ±5% for at least 30 minutes.

9. The method for producing an unsaturated carboxylic ester according to claim 8, wherein the unsaturated carboxylic acid and the alcohol are continuously fed to the reactor from the inlet of the reactor after the fluctuation width of the internal temperature of the reactor is kept at 0.5° C. or lower for at least 30 minutes.

\* \* \* \* \*